(12) United States Patent
Myerson

(10) Patent No.: US 10,781,484 B1
(45) Date of Patent: Sep. 22, 2020

(54) METHOD OF OLIGONUCLEOTIDE ANALYSIS

(71) Applicant: Agilent Technologies, Inc., Santa Clara, CA (US)

(72) Inventor: Joel Myerson, Berkeley, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 767 days.

(21) Appl. No.: 15/425,890

(22) Filed: Feb. 6, 2017

Related U.S. Application Data

(63) Continuation of application No. 15/269,214, filed on Sep. 19, 2016, now abandoned.

(60) Provisional application No. 62/235,470, filed on Sep. 30, 2015, provisional application No. 62/354,448, filed on Jun. 24, 2016.

(51) Int. Cl.
*C12Q 1/6872* (2018.01)

(52) U.S. Cl.
CPC .................................. *C12Q 1/6872* (2013.01)

(58) Field of Classification Search
CPC .................................................... C12Q 1/6872
See application file for complete search history.

(56) References Cited

U.S. PATENT DOCUMENTS

| 9,640,376 B1* | 5/2017 | Becker ............... H01J 49/0036 |
| 2011/0137022 A1* | 6/2011 | Michaud ............. C12Q 1/6806 536/25.34 |
| 2012/0322093 A1 | 12/2012 | Koll et al. |

OTHER PUBLICATIONS

Lietard et al. "Base-cleavable microarrays for the characterization of DNA and RNA oligonucleotides synthesized in situ by photolithography" Chem. Commun. 2014, 50, 12903-12906.

Tretyakova et al. "Mass Spectrometry of Structurally Modified DNA" Chem Rev. 2013, 113(4): 2395-2436.

* cited by examiner

*Primary Examiner* — Brian R Gordon
*Assistant Examiner* — Dwan A Gerido
(74) *Attorney, Agent, or Firm* — Stinson LLP

(57) ABSTRACT

Described herein, among other things, is a method of estimating efficiency of an oligonucleotide synthesis reaction. In some embodiments, the method comprises subjecting the products of one or more oligonucleotide synthesis reactions to LC-MS to produce a series of mass spectra, analyzing the mass spectra, and estimating the overall efficiency of an oligonucleotide synthesis reaction and/or the efficiency of addition of one or more of G, A, T or C individually in an oligonucleotide synthesis reaction.

17 Claims, 5 Drawing Sheets

Specification includes a Sequence Listing.

SEQUENCE LISTING

```
<160> NUMBER OF SEQ ID NOS: 1

<210> SEQ ID NO 1
<211> LENGTH: 30
<212> TYPE: DNA
<213> ORGANISM: Artificial Sequence
<220> FEATURE:
<223> OTHER INFORMATION: Synthetic nucleic acid

<400> SEQUENCE: 1
caactcgatg actcggctca gtcgatagat                                      30
```

US 10,781,484 B1

METHOD OF OLIGONUCLEOTIDE ANALYSIS

CROSS-REFERENCING

This application is a continuation of U.S. patent application Ser. No. 15/269,214, filed on Sep. 19, 2016, which claims the benefit of provisional application Ser. Nos. 62/235,470, filed on Sep. 30, 2015, and 62/354,448, filed on Jun. 24, 2016, all of which applications are incorporated by reference herein in their entireties.

BACKGROUND

In many technologies, including synthetic biology, the quality of synthetic oligonucleotides is paramount. For example, when synthetic genes are created from multiple oligonucleotides using a variety of existing processes, the presence of single base deletions will result in a frame shift, creating a non-functional gene. It is highly desirable to be able to measure the single base deletion rate of a particular oligonucleotide synthesis method.

SUMMARY

Described herein, among other things, is a method of estimating efficiency of an oligonucleotide synthesis reaction. In some embodiments, the method comprises subjecting the products of one or more oligonucleotide synthesis reactions to LC-MS to produce a series of mass spectra, analyzing the mass spectra, and estimating the overall efficiency of an oligonucleotide synthesis reaction and/or the efficiency of addition of one or more of G, A, T or C individually in an oligonucleotide synthesis reaction.

Depending on how the method is implemented, the method is rapid, accurate and does not involve DNA sequencing. Moreover, the method can provide both overall average single base deletion rates, as well as single base deletion rates for the individual nucleotides.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
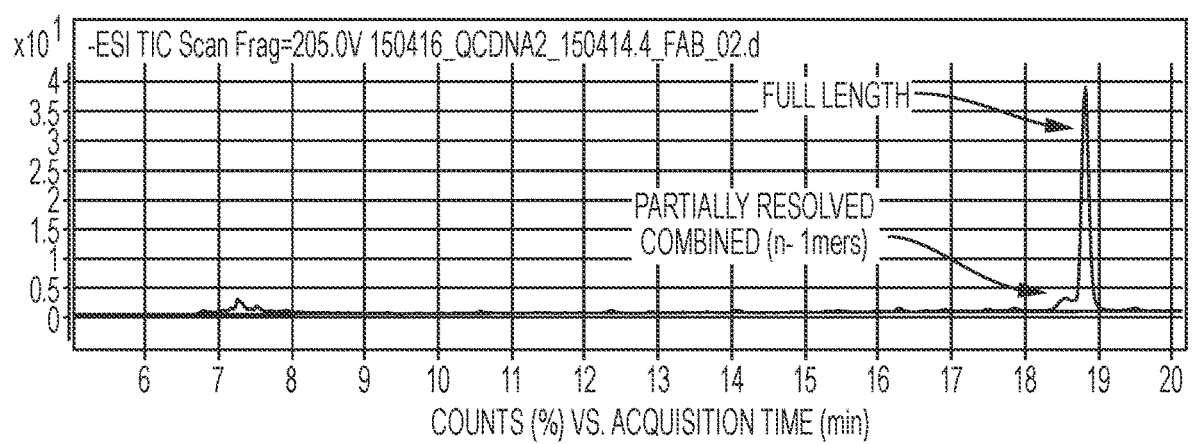
FIG. 1 shows the total ion current of an oligonucleotide synthesis reaction analyzed by LC-MS. SEQ ID NO:1.

Before describing exemplary embodiments in greater detail, the following definitions are set forth to illustrate and define the meaning and scope of the terms used in the description. Numeric ranges are inclusive of the numbers defining the range. Unless otherwise indicated, nucleic acids are written left to right in 5' to 3' orientation. The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in textbooks such as Gait, "*Oligonucleotide Synthesis: A Practical Approach*" 1984, IRL Press, London, Nelson and Cox (2000), Piet Herdewijn *Oligonucleotide Synthesis: Methods and Applications* 2005 Ed. Humana Press and Lehninger, A., *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "oligonucleotide" refers to a synthetically-made multimer of nucleotides of 2 to 500 nucleotides, e.g., 2 to 200 nucleotides in length. An oligonucleotide can be, e.g., 5 to 20, 21 to 30, 31 to 40, 41 to 50, 51-60, 61 to 70, 71 to 80, 80 to 100, 100 to 150 or 150 to 250 nucleotides in length. A single oligonucleotide may contain all four nucleotides (G, A, T and C) or any combination of the same (e.g., G, A, T or C, or any combination thereof). In an oligonucleotide, nucleotides may be linked together via phosphodiester bonds, but other linkages may be used.

As used herein, the term "oligonucleotide synthesis reaction" refers to a reaction in which oligonucleotides are chemically synthesized by adding monomers, e.g., protected phosphoramidites of natural nucleosides, one by one onto a growing chain. The nucleosides may be added to the 3' or the 5' end of the growing chain.

As used herein, the term "estimating" may be used interchangeably with the terms "determining", "measuring", "evaluating", "assessing," "assaying," and "analyzing" to refer to any form of measurement, and include determining if an element is present or not. These terms include both quantitative and/or qualitative determinations. Estimating may be relative or absolute.

As used herein, the term "full length oligonucleotide" refers to the oligonucleotide that an oligonucleotide synthesis reaction is designed to make. For example, if an oligonucleotide synthesis reaction has 30 coupling cycles, then the product of full length oligonucleotide will normally have 30 nucleotides (where, in the first cycle, the terminal nucleotide is coupled to a support).

As used herein, the term "n−1 reaction products" refers to a population of oligonucleotides made in an oligonucleotide synthesis reaction that are missing a single nucleotide monomer somewhere in their length. Relative to the full length oligonucleotide, each n−1 reaction product may be missing a single G, a single A, a single T or a single C, for example.

As used herein, the term "individual n−1 reaction products" refers to n−1 reaction products that are missing a particular type of nucleotide monomer, e.g., a G, A, T or C. For example, in a synthesis reaction of an oligonucleotide that is composed of G, A, T and C, one set of individual n−1 reaction products lack a single G, one set of individual n−1 reaction products lack a single A, one set of individual n−1 reaction products lack a single T, and one set of individual n−1 reaction products lack a single C.

As used herein, the term "liquid chromatography-mass spectrometry (LC-MS)" refers to a method in which the reaction products are subjected to liquid chromatography in an LC system and the products exiting the chromatography column are ionized and analyzed by mass spectrometry. The output of the LC is coupled to the ion source of the mass spectrometer system. The products exiting the LC are analyzed by mass spectrometry over a period of time.

As used herein, the term "plotting" refers to drawing a graph showing the relationship between two or more variables.

As used herein, the term "extracted ion chromatogram" refers to a chromatogram in which one or more m/z values representing one or more analytes of interest are recovered ('extracted') from the entire data set for a chromatographic run. See Murray et al "Definitions of terms relating to mass spectrometry (IUPAC Recommendations 2013). Pure and Applied Chemistry: 2013". In an extracted ion chromatogram, the total intensity or base peak intensity within a mass tolerance window around a particular analyte's mass-to-charge ratio is plotted over time.

As used herein, the term "m/z values in the mass spectra that correspond to" refers to data identified as being from one or more ions of a particular oligonucleotide, e.g., a full length oligonucleotide or a predicted n−1 product.

As used herein, the term "combined mass spectrum" refers to the product of combining a plurality of mass spectra. For example, if a first mass spectrum contains data for ion X and a second mass spectrum contains data for ion Y, then the combined mass spectrum will show data for both ion X and ion Y.

As used herein, the term "individual n−1 reaction products corresponding to a full length oligonucleotide missing G, A, T, or C" refers to the n−1 reaction products corresponding to a missing G, the n−1 reaction products corresponding to a missing A, the n−1 reaction products corresponding to a missing T, and the n−1 reaction products corresponding to a missing C, where those reaction products are independently resolvable by mass spectrometry.

As used herein, the terms "G", "A", "T" and "C" refer to nucleotides that contain guanine, adenine, thymine, and cytosine bases, respectively, as well as bases that base pair reliably with a complementary nucleotide. An oligonucleotide containing such nucleotides can be used as a template by a DNA or RNA polymerase. 7-deaza-adenine, 7-deaza-guanine, adenine, guanine, cytosine, thymine, uracil, 2-deaza-2-thio-guanine, 2-thio-7-deaza-guanine, 2-thio-adenine, 2-thio-7-deaza-adenine, isoguanine, 7-deaza-8-aza guanine, 7-deaza-8-aza-adenine, 5,6-dihydrouracil, 5,6-dihydrothymine, xanthine, 7-deaza-xanthine, hypoxanthine, 2,6 diamino-7-deaza purine, 5-methyl-cytosine, 5-propynyl-uracil, 5-propynyl-cytosine, 2-thio-thymine or 2-thio-uracil are examples of such bases, although others are known.

As used herein, the term "separately integrating the peaks corresponding to the full length oligonucleotide and the individual n−1 reaction products" refers to calculations that are done independently from one another and produce separate results for each of the full length oligonucleotide, the n−1 reaction products corresponding to a missing G, the n−1 reaction products corresponding to a missing A, the n−1 reaction products corresponding to a missing T, and the n−1 reaction products corresponding to a missing C.

As used herein, the term "total ion chromatogram" refers to a chromatogram in which the total number of ions detected is plotted over time. A total ion chromatogram may be derived from the total ion current of a detector. See Murray et al "Definitions of terms relating to mass spectrometry (IUPAC Recommendations 2013). Pure and Applied Chemistry: 2013".

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Provided herein is a method of estimating efficiency of an oligonucleotide synthesis reaction. In some embodiments, the method may comprise: (a) subjecting the products of one or more oligonucleotide synthesis reactions to liquid chromatography-mass spectrometry (LC-MS) to produce a series of mass spectra; (b) identifying, in the mass spectra of (a) or a combined mass spectrum of the same, m/z values that correspond to: i. one or more full length oligonucleotides; and ii. individual n−1 reaction products corresponding to a full length oligonucleotide missing G, A, T, or C; (c) analyzing the m/z values identified in step (b) to provide estimates of i. the amount of the full length oligonucleotide and ii. the amount of the n−1 reaction products, either collectively or individually, in the one or more oligonucleotide synthesis reactions; and (d) estimating, using the results of (c): i. the overall efficiency of an oligonucleotide synthesis reaction and/or ii. the efficiency of addition of one or more of G, A, T or C individually in an oligonucleotide synthesis reaction.

In embodiments that rely on plotting an extracted ion chromatogram, steps (b) and (c) of the method may comprise plotting an extracted ion chromatogram for m/z values in the mass spectra of (a) that correspond to the full length oligonucleotide and the individual n−1 reaction products corresponding to a missing G, A, T, or C, and separately integrating the peaks corresponding to the full length oligonucleotide and the individual n−1 reaction products in the extracted ion chromatogram, thereby providing the estimates of (c). In these embodiments, the method may comprise: (a) subjecting the products of one or more oligonucleotide synthesis reactions to liquid chromatography-mass spectrometry (LC-MS) to produce a series of mass spectra; (b) identifying, in the mass spectra of (a) m/z values that correspond to: i. one or more full length oligonucleotides; and ii. individual n−1 reaction products corresponding to a full length oligonucleotide missing G, A, T, or C; (c) plotting an extracted ion chromatogram for m/z values in the mass spectra of (a) that correspond to the full length oligonucleotide and the individual n−1 reaction products corresponding to a missing G, A, T, or C, and separately integrating the peaks corresponding to the full length oligonucleotide and the individual n−1 reaction products in the extracted ion chromatogram to provide estimates of i. the amount of the full length oligonucleotide and ii. the amount of the n−1 reaction products, either collectively or individually, in the one or more oligonucleotide synthesis reactions; and (d) estimating, using the results of (c): i. the overall efficiency of an oligonucleotide synthesis reaction and/or ii. the efficiency of addition of one or more of G, A, T or C individually in an oligonucleotide synthesis reaction.

In embodiments that rely on plotting a total ion chromatogram, steps (b) and (c) of the method may comprise: i. plotting a total ion chromatogram; ii. combining the mass spectra corresponding to a window of the total ion chromatogram to produce the combined mass spectrum, wherein the window corresponds to the full length (FL) and n−1 products; and iii. integrating m/z values in the combined mass spectrum that correspond to the full length oligonucleotide and the n−1 reaction products, thereby providing the estimates of (c). In these embodiments, the method may comprise: (a) subjecting the products of one or more oligonucleotide synthesis reactions to liquid chromatography-mass spectrometry (LC-MS) to produce a series of mass spectra; (b) i. plotting a total ion chromatogram; ii. combining the mass spectra corresponding to a window of the total ion chromatogram to produce the combined mass spectrum, wherein the window corresponds to the FL and n−1 products; and (c) integrating m/z values in the combined mass spectrum that correspond to the full length oligonucleotide and the n−1 reaction products to provide estimates of i. the amount of the full length oligonucleotide and ii. the amount of the n−1 reaction products, either collectively or individually, in the one or more oligonucleotide synthesis reactions; and (d) estimating, using the results of (c): i. the overall efficiency of an oligonucleotide synthesis reaction and/or ii. the efficiency of addition of one or more of G, A, T or C individually in an oligonucleotide synthesis reaction.

In some embodiments, the method may be done on a single oligonucleotide synthesis reaction, wherein the full length oligonucleotide synthesized in step (a) comprises G, A, T and C. In this embodiment, the method may comprise analyzing the m/z values corresponding to all four n−1 products of a single synthesis reaction, and estimating i. the amount of the full length oligonucleotide and ii. the amount of the n−1 reaction products, either collectively or individually, in the one or more oligonucleotide synthesis reactions.

In other embodiments, the method may be done on multiple oligonucleotide synthesis reactions, wherein the full length oligonucleotide synthesized in step (a) lacks a G, A, T or C, or any combination thereof, and (ii) collectively, the full length oligonucleotides comprise G, A, T and C. To illustrate by example, in some cases, the method may be performed on four oligonucleotides (oligo-dT, oligo-dA, oligo-dG and oligo-dC). These oligonucleotides each lack the full complement of nucleotides (i.e., the oligo-dT lacks G, A and C, etc.) and collectively comprise the full complement of nucleotides (G, A, T and C). In another example, the method may be performed on two oligonucleotides (e.g., one oligonucleotide containing G's and A's and another oligonucleotide containing T's and C's, etc.). These oligonucleotides, individually, lack the full complement of nucleotides (i.e., "GA" oligonucleotide lacks T and C, etc.) and collectively comprise the full complement of nucleotides (G, A, T and C).

As would be apparent, the m/z values of step (b) may identified by identifying which m/z values in the mass spectra correspond to molecular formulas corresponding to the full length oligonucleotide and the predicted individual n−1 reaction products. This may be done using Agilent's "MassHunter" software and equivalents thereof.

The estimates produced in the method may be used to calculate various parameters relating to the efficiency of an oligonucleotide synthesis reaction. In some embodiments, the method may comprise calculating the overall efficiency of an oligonucleotide synthesis reaction, where the term "overall efficiency" refers to the percentage of full length oligonucleotide relative to the amount of full length oligonucleotide and n−1 reaction products in a synthesis reaction. In another embodiment, the method may further comprise calculating the overall cycle yield of an oligonucleotide synthesis reaction, where the term "overall cycle yield" refers to the percentage of n+1 products relative to the amount of n+1 product (a product to which a nucleotide has been added) and n+0 product (a product to which a nucleotide not been added) made during each cycle of a synthesis reaction. In another embodiment, the method may further comprise calculating the singe base deletion rate of an oligonucleotide synthesis reaction, where the term "single base deletion rate" refers to the rate at which an oligonucleotide synthesis reaction fails to add a monomer, expressed in a per nucleotide basis. For example, an oligonucleotide synthesis reaction that has an overall cycle yield of 98% has a single base deletion rate of 1 in 50.

In addition to estimating overall efficiency and yield, etc., the method may be used to calculate the individual cycle yield for one or more of G, A, T and C (i.e., G, A, T or C, or any combination thereof) in an oligonucleotide synthesis reaction, where the term "individual cycle yield for one or more of G, A, T and C" refers to the percentage of product that contains an added G, A, T or C in a synthesis cycle in which that nucleotide is added. For example, if the individual cycle yield for a G is 99%, then 99% of the products contain an added G at the end of a G addition cycle. Finally, some embodiments may comprise calculating the individual base deletion rate for one or more of G, A, T and C in an oligonucleotide synthesis reaction. This metric provides an indication of the rate at which an oligonucleotide synthesis reaction fails to add a particular monomer, i.e., a G, A, T or C, expressed in a per nucleotide basis. For example, an oligonucleotide synthesis reaction that has a single base deletion rate for G of 1 in 100 is a reaction in which the reaction fails to add a G at a rate or 1 in 100 Gs.

The chemistry used in the oligonucleotide synthesis reaction may vary. In general terms, oligonucleotide synthesis is a stepwise process in which one nucleotide is added after another onto a growing chain. Oligonucleotide synthesis is commonly performed using solid phase phosphoramidite chemistry, although other chemistries are known. Oligonucleotide synthesis is reviewed in a variety of publications, including Beaucage et al (Advances in the Synthesis of Oligonucleotides by the Phosphoramidite Approach Tetrahedron 1992 48 (12): 2223), Brown (A brief history of oligonucleotide synthesis. Methods in Molecular Biology 1993, 20 Protocols for Oligonucleotides and Analogs, 1-17), Reese (Oligo- and poly-nucleotides: 50 years of chemical synthesis". Organic & Biomolecular Chemistry 2005 3: 3851) and Iyer (Oligonucleotide synthesis. In: Comprehensive Natural Products Chemistry, Vol. 7: DNA and Aspects of Molecular Biology. Kool, Eric T.; Editor. Neth. (1999), Elsevier, Amsterdam, pp. 105-152). Such methods include photolithographic methods, as well as drop deposition methods. In some embodiments, oligonucleotides may be made on a solid support in the form of an array. See, e.g., Cleary et al. (Nature Methods 2004 1: 241-248) and LeProust et al. (Nucleic Acids Research 2010 38: 2522-2540).

In general, oligonucleotide synthesis typically involves three steps:

1. A coupling step, in which an activated phosphoramidite is coupled on to the free 5'-hydroxyl of the growing oligonucleotide chain. This results in a phosphite triester, with a protected 5'-hydroxyl at the end.

2. An oxidation step, in which the phosphite triester is oxidized to the more stable phosphate triester.

3. A deblock step, in which the protecting group on the 5'-hydroxyl is removed, creating a new free 5'-hydroxyl.

Many protocols also incorporate a capping step in which unreacted 5'-hydroxyl is capped after the coupling step, e.g., as an acetate, in order to prevent further extension.

This process is repeated until the oligonucleotide is of the desired length. After the oligonucleotide is made, it is cleaved off of the solid phase and the protecting groups on the nucleoside bases and the backbone are removed.

There are several variations of this method. For example, in some methods the oligonucleotide is synthesized in reverse, i.e., from the 5'- to the 3' end. In another example, the optional capping step may be done both before and after oxidation.

In some embodiments, the one or more oligonucleotide synthesis reactions may be capping-free reactions (oligonucleotide synthesis reactions that do not have a capping step in which unreacted 5'-hydroxyls are capped, e.g., as an acetate, in order to prevent further addition). In other embodiments, the one or more oligonucleotide synthesis reactions comprise a capping step. The one or more oligonucleotides analyzed in the method may be of any particular length, e.g., 8 to 100 nucleotides, e.g., 10 to 60 nucleotides, although oligonucleotides outside of this range may be analyzed without undue effort.

As would be apparent, the liquid chromatography may be done by high performance liquid chromatography (HPLC), which term is intended to encompass chromatography methods in which a liquid solvent containing the product of an oligonucleotide synthesis is passed through a column filled with a solid adsorbent material under pressure (e.g., of at least 10 bar, e.g., 50-350 bar). The output of the liquid chromatography column is operably linked to a suitable ion source (e.g., an electrospray ion source, although other sources can be used) and the ions produced may be analyzed by time of flight mass spectrometry (although, again, a variety of other mass spectrometry methods may be used). The mass spectra should be obtained for at least the entire period in which the full length oligonucleotide and n−1 mers elute from the column. This period may be in the range of about 1 sec to 3 min, e.g., 2 sec to 30 sec, 5 sec to 20 sec or 10 sec to 2 min (see, e.g., FIG. 6). The rate at which the mass spectra are obtained may be in the range of 0.1/sec to 1000/sec, although this number can vary greatly depending on how much resolution is required.

The method described above may be generally employed to analyze the efficiency of an oligonucleotide synthesis reaction and, in some embodiments, can be used to compare the efficiency of two different oligonucleotide synthesis reactions. In these embodiments, the method may comprise: (a) using the present method to analyze a first oligonucleotide synthesis reaction and a second oligonucleotide synthesis reaction, wherein the first and second oligonucleotide synthesis reactions can be performed under different conditions or at different times, for example; and (b) comparing the results obtained in step (a). For example, the first and second oligonucleotide synthesis reactions may differ in the reagents used and/or the timing or temperature of each step, or as a quality control measure to ensure that the efficiency of oligonucleotide synthesis has not been changed over time. The present method may be used to optimize the conditions for oligonucleotide synthesis.

As would be apparent, after LC-MS, the steps of the above-described method can be implemented on a computer. In certain embodiments, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer that runs the program and returns an output to the user.

A system can, in certain embodiments, comprise a computer that includes: a) a central processing unit; b) a main non-volatile storage drive, which can include one or more hard drives, for storing software and data, where the storage drive is controlled by disk controller; c) a system memory, e.g., high speed random-access memory (RAM), for storing system control programs, data, and application programs, including programs and data loaded from non-volatile storage drive; system memory can also include read-only memory (ROM); d) a user interface, including one or more input or output devices, such as a mouse, a keypad, and a display; e) an optional network interface card for connecting to any wired or wireless communication network, e.g., a printer; and f) an internal bus for interconnecting the aforementioned elements of the system.

The memory of a computer system can be any device that can store information for retrieval by a processor, and can include magnetic or optical devices, or solid state memory devices (such as volatile or non-volatile RAM). A memory or memory unit can have more than one physical memory device of the same or different types (for example, a memory can have multiple memory devices such as multiple drives, cards, or multiple solid state memory devices or some combination of the same). With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, floppy disk and DVD are all examples of permanent memory. Random Access Memory (RAM) is an example of non-permanent (i.e., volatile) memory. A file in permanent memory can be editable and re-writable.

Operation of the computer is controlled primarily by an operating system, which is executed by the central processing unit. The operating system can be stored in a system memory. In some embodiments, the operating system includes a file system. In addition to an operating system, one possible implementation of the system memory includes a variety of programming files and data files for implementing the method described below. In certain cases, the programming can contain a program, where the program can be composed of various modules, and a user interface module that permits a user to manually select or change the inputs to or the parameters used by the program. The data files can include various inputs for the program.

In order to further illustrate the present invention, the following specific examples are given with the understanding that they are being offered to illustrate the present invention and should not be construed in any way as limiting its scope.

EXAMPLES

Aspects of the present teachings can be further understood in light of the following example, which should not be construed as limiting the scope of the present teachings in any way.

Example 1

Analysis Using an Extracted Ion Chromatogram

The following methods provide both overall average single base deletion rates, as well as single base deletion rates for the individual nucleotides A, C, G, and T.

Using mass spectrometry to compare the amount of (n−1)mer created with the amount of full length material observed, overall and individual cycle yields can be obtained, and from this a single base deletion rate can be determined. HPLC of shorter oligos can separate the (n−1) mers from the full length material. The total ion chromatogram of the products obtained from the synthesis of a 30mer (SEQ ID NO: 1)
CAACTCGATGACTCGGCTCAGTCGATAGAT is shown in FIG. 1.

The (n−1)mers need not be completely separated by HPLC because the mass spectrometer is capable of creating extracted ion chromatograms, in which only the compounds of interest are visualized. This can be done manually by creating EICs of selected ions, or the extraction of the ion chromatograms can be assisted by the use of software programs, e.g by using the Find by Formula algorithm in the MassHunter software. In this way, a large number of the ion charge states are used to create the extracted ion chromatogram. Typical ion charge states for a 30mer oligonucleotide, along with their m/z values, are shown in FIG. 2.

Figure 2:
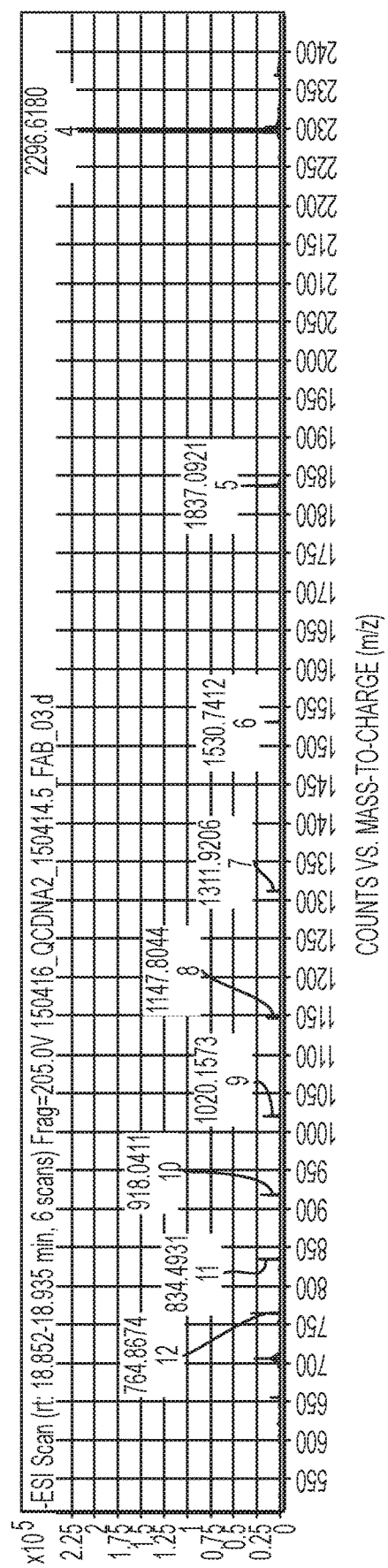
FIG. 2 shows the m/z values for a full length oligonucleotide.
Figure 3:
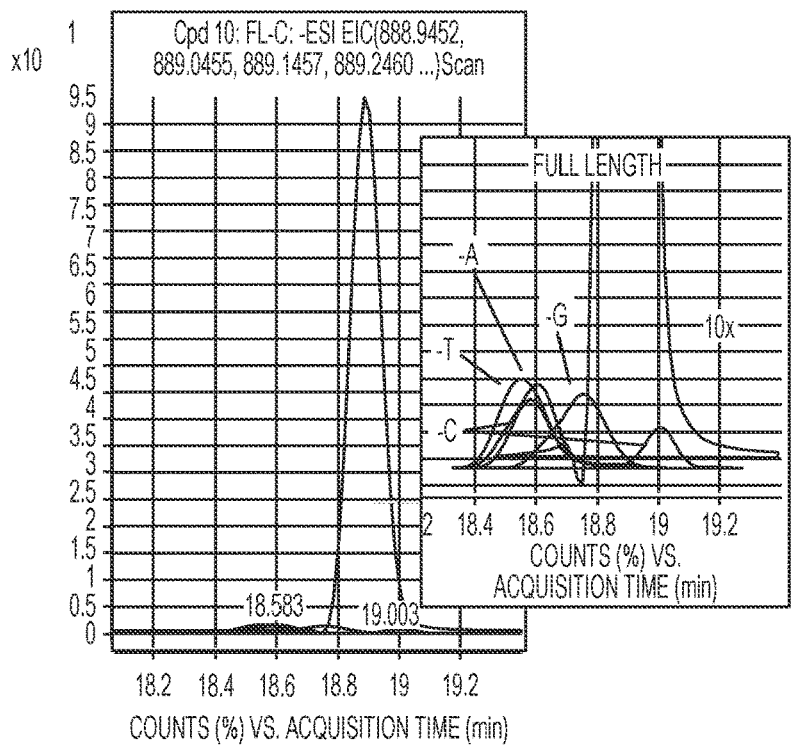
FIG. 3 shows the extracted ion chromatograms for m/z values corresponding to a full length oligonucleotide, and the individual n−1 reaction products corresponding to a missing G, A, T, or C, for an oligonucleotide synthesis reaction for an oligonucleotide reaction with a 99.68% cycle yield and no capping steps.

The extracted ion chromatograms are created for all four possible (n−1)mers, shown superimposed in FIG. 2. In these chromatograms, the original full length and the individual full length minus A, C, G, and T are visible, and can be readily quantitated by integration. The amount of (n−2)mer formed from single base deletions present in the (n−1)mer (and so on) are present at levels too low to measure accurately, but can be mathematically modeled to a binomial distribution. The calculated cycle yield can be obtained using the equation:

$$\text{Cycle yield} = n*F/(n*F+M)$$

where
n=length of oligo
F=amount of full length oligo
M=amount of (n−1)mer oligo In the example shown in FIG. 3, applying this formula gives a calculated cycle yield of about 99.68%. The single base deletion rate can be calculated from the cycle yield using the equation:

$$\text{Single base deletion rate} = 1/(1-\text{cycle yield})$$

which results in a calculated single base deletion rate of 1 in 312. This means that on average, one out of every 312 nucleotides synthesized will be missing due to a failure to couple, deblock, or if capping is used, a failure to cap.

Cycle yields per base (B=G, A, T or C), can be calculated using the following formula:

Cycle yield $B = nB*F/(nB*F+mB)$

Where
nB=number of a particular base (A, T, C, or G) present in the full length oligo
F=amount of full length oligo
mB=amount of full length oligo missing base a single base B In the example above, the individual base cycle yields calculated were

| Individual base yields | Cycle Yield | Freq (1 in) |
|---|---|---|
| G | 99.68% | 317 |
| T | 99.62% | 266 |
| A | 99.71% | 350 |
| C | 99.69% | 323 |

Figure 4:
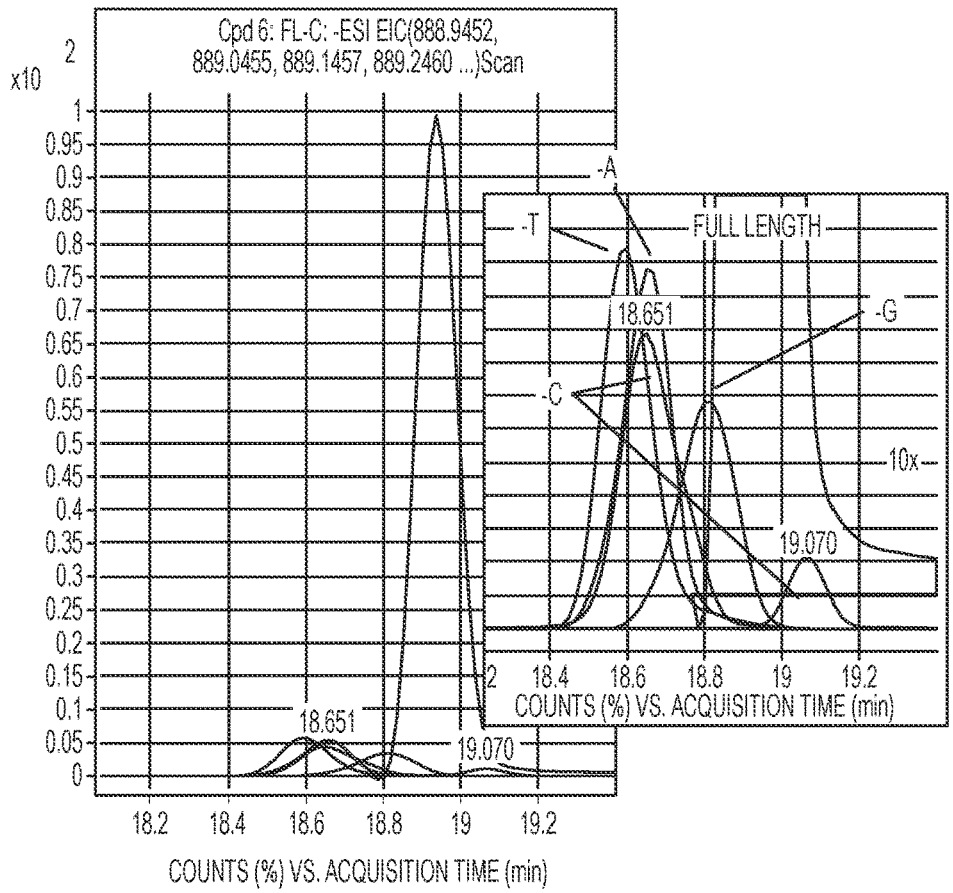
FIG. 4 shows the extracted ion chromatograms for m/z values corresponding to a full length oligonucleotide, and the individual n−1 reaction products corresponding to a missing G, A, T, or C, for an oligonucleotide synthesis reaction with a 99.14% cycle yield and no capping steps.

In the examples shown in FIGS. 3 and 4, no capping was performed. This may be advantageous for certain applications. In addition, the absence of capping creates a larger amount of (n−1)mers, which makes the measurement using HPLC-MS more accurate.

The ability to differentiate between differences in oligonucleotide synthesis efficiency is shown below. In this example, the cycle yield was worse than the example shown in FIG. 3:

Analysis of the chromatogram shown in FIG. 4 shows that the calculated cycle yield is about 99.14%, or a single base deletion rate of 1 in 117. In this example, the individual base cycle yields calculated were:

| Individual base yields | Cycle Yield | Freq (1 in . . .) |
|---|---|---|
| G | 99.32% | 147 |
| T | 98.98% | 98 |
| A | 99.17% | 120 |
| C | 99.10% | 111 |

This method can be used for oligonucleotides longer or shorter than 30. For highly efficient syntheses (>99.9% cycle yield), the use of longer oligonucleotides should result in a larger cumulative (n−1) peak, enabling a more accurate measurement. For best results, good isotopic resolution is desired, and the longer the oligonucleotide the less resolved individual isotopes will be. The HPLC should be able to separate the (n−1)mer from the full length, although this is mitigated to some extent by the ability of the mass spectrometer to do extracted ion chromatograms of overlapping spectra.

Figure 5:
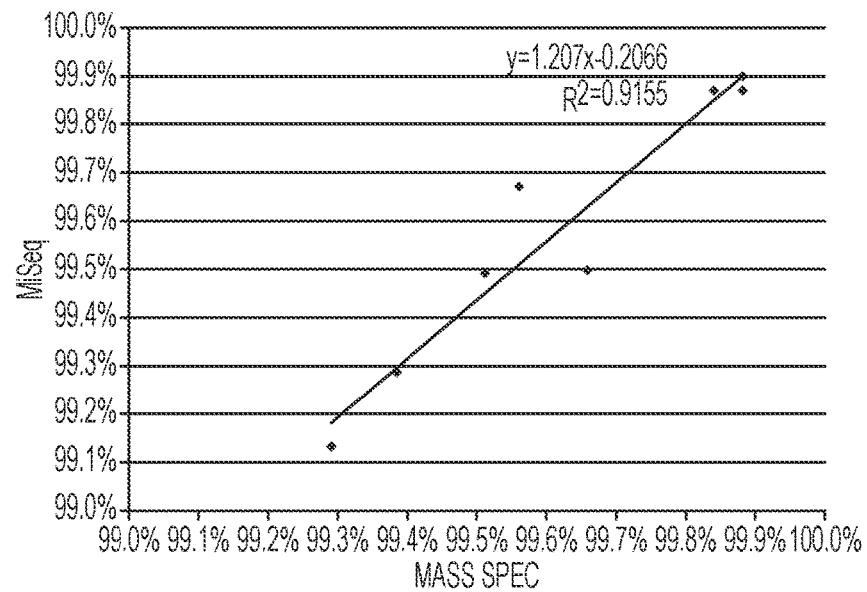
FIG. 5 is a graph showing a comparison of the cycle yields of a series of oligonucleotide synthesis reactions, as determined by Illumina sequencing and the present method.

The mass spec method described was compared to the cycle yields determined by Illumina sequencing. As shown in the graph of FIG. 5, good agreement was obtained.

Example 2

Analysis Using a Total Ion Chromatogram

As an alternative to creating an extracted ion chromatogram (EIC) and integrating the EIC peaks to determine the amounts of full length and (n−1)mers, direct integration of the mass spectra can also be used.

Figure 6:
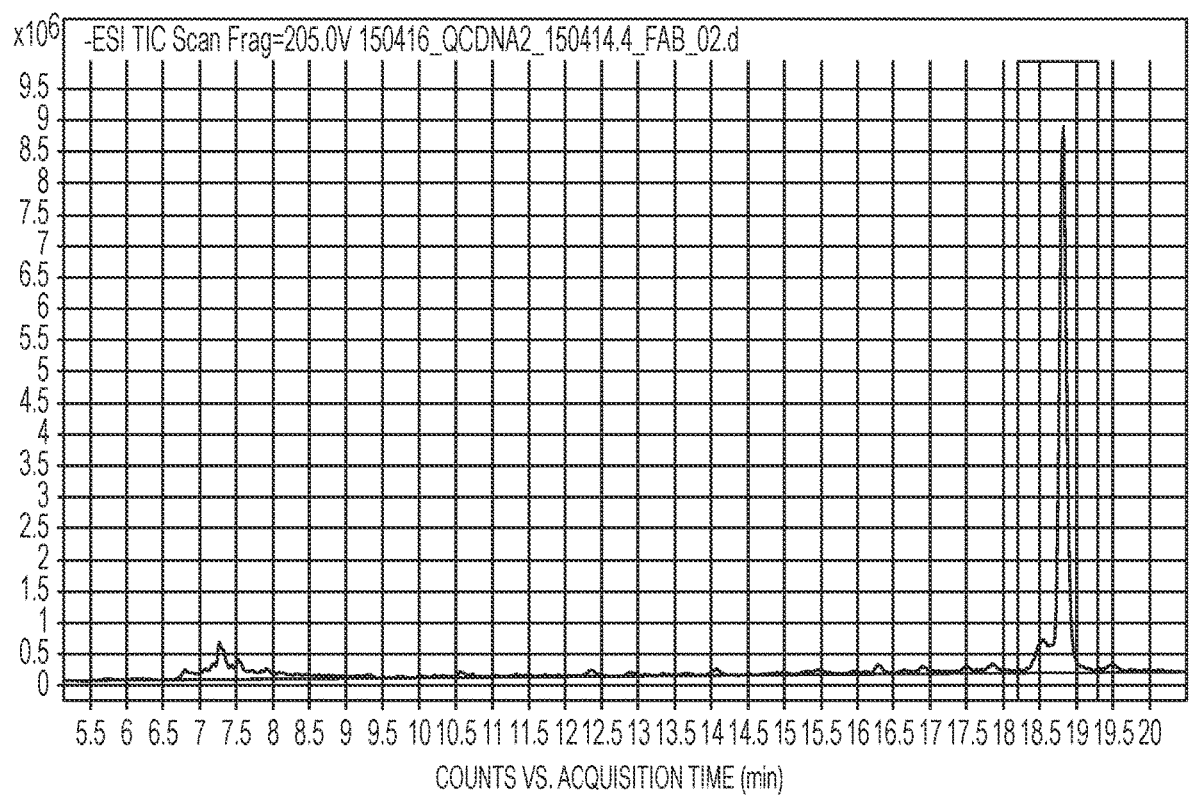
FIG. 6 shows the total ion current of an oligonucleotide synthesis reaction analyzed by LC-MS.

After chromatography, the combined mass spectra containing the full length and the (n−1) peaks are extracted from a window of the TIC (total ion chromatogram), as shown in FIG. 6.

Figure 7:
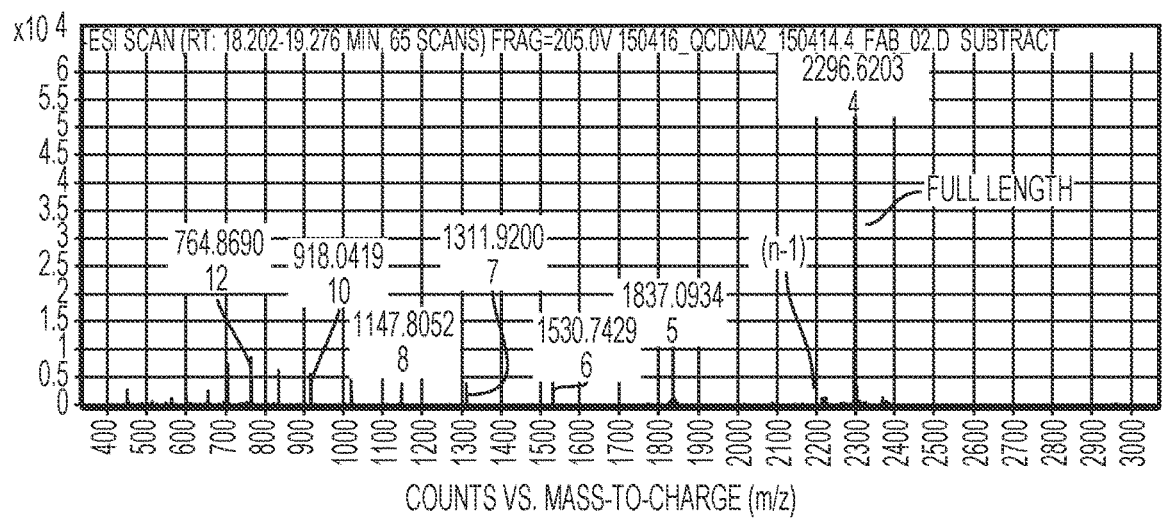
FIG. 7 shows a combined mass spectrum corresponding to the window of the total ion chromatogram shown in FIG. 6.

The resulting mass spectrum (FIG. 7) contains multiply charged ions for the full length and all of the (n−1) compounds. In the spectrum below, only the [−4] charge state is clearly visible, but if the y-axis is expanded, the m/z corresponding to (n−1) compounds at other charge states are also visible.

While it is possible to determine the individual base yields by this method, it is not shown here.

Figure 8:
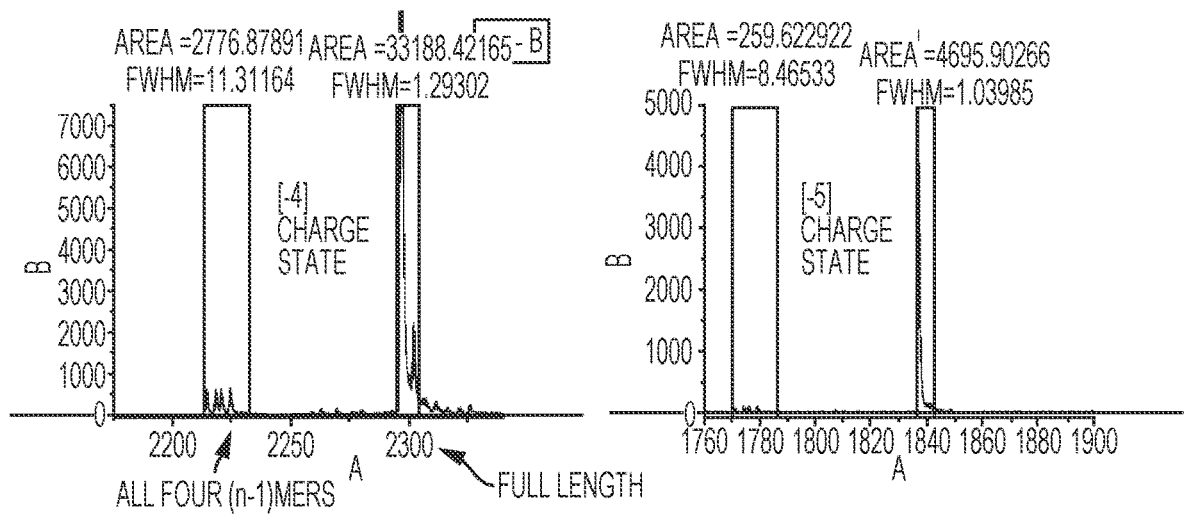
FIG. 8 shows the integrated areas of the [−4] and [−5] charge states for the full length and n−1 reaction products in the mass spectrum shown in FIG. 7.

As shown in FIG. 8, adding up the integrated areas for the [−4] and [−5] charge states gives a calculated overall cycle yield based on all of the combined (n−1)mers, in this case indicating a 99.72% cycle yield. The extracted ion chromatogram method gave a calculated yield of 99.68%. In this example, the direct mass spec integration method did not average all of the ions, and EICs are probably closer to actual yield.

Exemplary Embodiments

A method of estimating efficiency of an oligonucleotide synthesis reaction, comprising: (a) subjecting the products of one or more oligonucleotide synthesis reactions to liquid chromatography-mass spectrometry (LC-MS) to produce a series of mass spectra; (b) identifying, in the mass spectra of (a) or a combined mass spectrum of the same, m/z values that correspond to: i. one or more full length oligonucleotides; and ii. individual n−1 reaction products corresponding to a full length oligonucleotide missing G, A, T, or C; (c) analyzing the m/z values identified in step (b) to provide estimates of i. the amount of the full length oligonucleotide and ii. the amount of the n−1 reaction products, either collectively or individually, in the one or more oligonucleotide synthesis reactions; and (d) estimating, using the results of (c): i. the overall efficiency of an oligonucleotide synthesis reaction and/or ii. the efficiency of addition of one or more of G, A, T or C individually in an oligonucleotide synthesis reaction.

In any embodiment, the oligonucleotide reaction may comprise a coupling step (e.g., in which an activated phosphoramidite is coupled on to the free hydroxyl of the growing oligonucleotide chain), an oxidation step in which the phosphite triester produced in the prior step is oxidized to the more stable phosphate trimester, and a deblocking step in which the protecting group on the hydroxyl is removed, creating a new free hydroxyl. In any embodiment, the hydroxyl may be a 5' hydroxyl. In any embodiment, the hydroxyl may be a 3' hydroxyl.

In any embodiment, steps (b) and (c) may be done by creating and analyzing an extracted ion chromatogram. In these embodiments, the method may comprise: i. plotting an extracted ion chromatogram for m/z values in the mass spectra of (a) that correspond to: i. the full length oligonucleotide; and ii. the individual n−1 reaction products corresponding to a missing G, A, T, or C; ii. separately integrating the peaks corresponding to the full length oligonucleotide and the individual n−1 reaction products in the extracted ion chromatogram, thereby providing the estimates of (c).

In any embodiment, step (b) and may be by creating and analyzing a total ion chromatogram. In these embodiments, the method may comprise: i. plotting a total ion chromatogram; ii. combining the mass spectra corresponding to a window of the total ion chromatogram to produce the combined mass spectrum, wherein the window corresponds to the FL and n−1 products; and iii. integrating or determining the height of the mass spectral peak in the combined mass spectrum corresponding to m/z values in the combined mass spectrum that correspond to the full length oligonucleotide and the n−1 reaction products. In any embodiment, the method may be done on a single oligonucleotide synthesis reaction, wherein the full length oligonucleotide of the reaction comprising G, A, T and C.

In any embodiment, the method may be done on multiple oligonucleotide synthesis reactions, wherein: (i) the full length oligonucleotide of each reaction lacks a G, A, T or C, or any combination thereof, and (ii) collectively, the full length oligonucleotides comprise G, A, T and C.

In any embodiment, the method may further comprise calculating the overall efficiency of an oligonucleotide synthesis reaction.

In any embodiment, the method may further comprise calculating the overall cycle yield of an oligonucleotide synthesis reaction.

In any embodiment, the method may further comprise calculating the singe base deletion rate of an oligonucleotide synthesis reaction.

In any embodiment, the method may further comprise calculating the individual cycle yield for one or more G, A, T and C in an oligonucleotide synthesis reaction.

In any embodiment, the method may further comprise calculating the individual base deletion rate for one or more of G, A, T and C in an oligonucleotide synthesis reaction.

In any embodiment, the one or more oligonucleotide synthesis reactions may be capping-free reactions.

In any embodiment, the one or more oligonucleotide synthesis reactions may comprise capping.

In any embodiment, the oligonucleotide may be 10 to 60 nucleotides in length.

In any embodiment, the mass spectra of (a) may be obtained at a rate in the range of 0.1/sec to 1000/sec.

In any embodiment, the liquid chromatography may be high performance liquid chromatography (HPLC).

In any embodiment, the mass spectrometry may be done by electrospray ionization-time of flight mass spectrometry (ESI-TOF).

A method comprising (a) using the method of any embodiment to analyze a first oligonucleotide synthesis reaction and a second oligonucleotide synthesis reaction, wherein the first and second oligonucleotide synthesis reactions are performed under different conditions; (b) comparing the results obtained in step (a).

(b) plotting an extracted ion chromatogram for m/z values in the mass spectra of (a) that correspond to: i. the full length oligonucleotide; and ii. individual n−1 reaction products corresponding to a missing G, A, T, or C;

(c) separately integrating peaks corresponding to the full length oligonucleotide and the individual n−1 reaction products in the extracted ion chromatogram, thereby providing the amount of the full length oligonucleotide and ii. the amount of the n−1 reaction products, either collectively or individually, in the one or more oligonucleotide synthesis reactions; and (d) estimating, using the results of (c): i. the efficiency of an oligonucleotide synthesis reaction and/or ii. the efficiency of addition of one or more of G, A, T or C individually in an oligonucleotide synthesis reaction.

2. The method of claim 1, wherein the method is done on a single oligonucleotide synthesis reaction, wherein the full length oligonucleotide of the reaction comprises G, A, T and C.

3. The method of claim 1, wherein the method is done on multiple oligonucleotide synthesis reactions, wherein: (i) the full length oligonucleotide of each reaction lacks a G, A, T or C, or any combination thereof, and (ii) collectively, the full length oligonucleotides comprise G, A, T and C.

4. The method of claim 1, further comprising calculating the overall efficiency of an oligonucleotide synthesis reaction.

5. The method of claim 1, further comprising calculating the overall cycle yield of an oligonucleotide synthesis reaction.

6. The method of claim 1, further comprising calculating the singe base deletion rate of an oligonucleotide synthesis reaction.

7. The method of claim 1, further comprising calculating the individual cycle yield for one or more G, A, T and C in an oligonucleotide synthesis reaction.

8. The method of claim 1, further comprising calculating the individual base deletion rate for one or more of G, A, T and C in an oligonucleotide synthesis reaction.

9. The method of claim 1, wherein the one or more oligonucleotide synthesis reactions are capping-free reactions.

10. The method of claim 1, wherein the one or more oligonucleotide synthesis reactions comprise capping.

The invention claimed is:

1. A method of estimating efficiency of an oligonucleotide synthesis reaction, comprising:

(a) subjecting the products of one or more oligonucleotide synthesis reactions to liquid chromatography-mass spectrometry (LC-MS) to produce a series of mass spectra;

11. The method of claim 1, wherein the one or more oligonucleotides are 10 to 60 nucleotides in length.

12. The method of claim 1, wherein the mass spectra of (a) are obtained at a rate in the range of 0.1/sec to 1000/sec.

13. The method of claim 1, wherein the liquid chromatography is high performance liquid chromatography (HPLC).

14. The method of claim 1, wherein the mass spectrometry is done by electrospray ionization-time of flight mass spectrometry (ESI-TOF).

15. A method comprising;
 (a) using the method of claim 1 to analyze a first oligonucleotide synthesis reaction and a second oligonucleotide synthesis reaction;
 (b) comparing the results obtained in step (a).

16. The method of claim 15, wherein the first and second oligonucleotide synthesis reactions are performed under different conditions.

17. The method of claim 15, wherein the first and second oligonucleotide synthesis reactions are performed at different times.

\* \* \* \* \*